United States Patent
Blum et al.

(10) Patent No.: US 7,510,313 B2
(45) Date of Patent: Mar. 31, 2009

(54) FIBEROPTIC ILLUMINATOR

(75) Inventors: Johannes M. Blum, Orange Park, FL (US); Walter Orozco, Jacksonville, FL (US); Eric A. VanDenhende, Jacksonville, FL (US); David Mutch, Jacksonville, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 149 days.

(21) Appl. No.: 11/626,101

(22) Filed: Jan. 23, 2007

(65) Prior Publication Data

US 2008/0175020 A1   Jul. 24, 2008

(51) Int. Cl.
*F21V 8/00* (2006.01)

(52) U.S. Cl. .............. 362/580; 362/551; 362/554; 362/581; 362/583

(58) Field of Classification Search .......... 362/551, 362/554, 580, 581, 583, 294
See application file for complete search history.

(56) References Cited

U.S. PATENT DOCUMENTS

| | | | |
|---|---|---|---|
| 4,770,948 A | 9/1988 | Oikawa et al. | |
| 5,243,500 A * | 9/1993 | Stephenson et al. | 362/580 |
| 5,295,052 A * | 3/1994 | Chin et al. | 362/580 |
| 5,301,090 A * | 4/1994 | Hed | 362/558 |
| 5,329,436 A | 7/1994 | Chiu | |
| 5,617,302 A * | 4/1997 | Kloots | 362/581 |
| 5,961,203 A | 10/1999 | Schuda | |
| 6,065,882 A | 5/2000 | Roller et al. | |
| 6,464,383 B1 | 10/2002 | Northington et al. | |
| 6,672,749 B2 * | 1/2004 | Nicholls et al. | 362/559 |
| 6,942,372 B1 | 9/2005 | Davis | |
| 7,057,345 B2 * | 6/2006 | Kikuchi et al. | 313/595 |
| 2001/0051763 A1 | 12/2001 | Kurosawa et al. | |
| 2006/0217787 A1 | 9/2006 | Olson et al. | |

OTHER PUBLICATIONS

Sunoptics, "SolarMaxx 300 Lightsource", 2 page printout from website, Dec. 2006 (admitted prior art).
Ushio, "Ceramic Xenon Lamps", 6 page printout from website, Dec. 2006 (admitted prior art).
PCT International Search Report and Written Opinion of the International Searching Authority issued in connection with corresponding International Patent Application No. PCT/US08/51751, mailing date of Sep. 17, 2008.

* cited by examiner

*Primary Examiner*—Sandra O'Shea
*Assistant Examiner*—James W Cranson
(74) *Attorney, Agent, or Firm*—Howson & Howson LLP

(57) ABSTRACT

A fiberoptic illuminator has a housing with an interface enabling an end fitting of a fiber optic bundle of a medical device to be connected to the housing. The illuminator includes a lamp assembly mounted within the housing for directing a high intensity beam of light through an optics assembly and into the fiber optic bundle. The lamp assembly includes a ceramic xenon lamp of greater than 300 watts. Preferably, the ceramic xenon lamp is at least 400 watts.

20 Claims, 4 Drawing Sheets

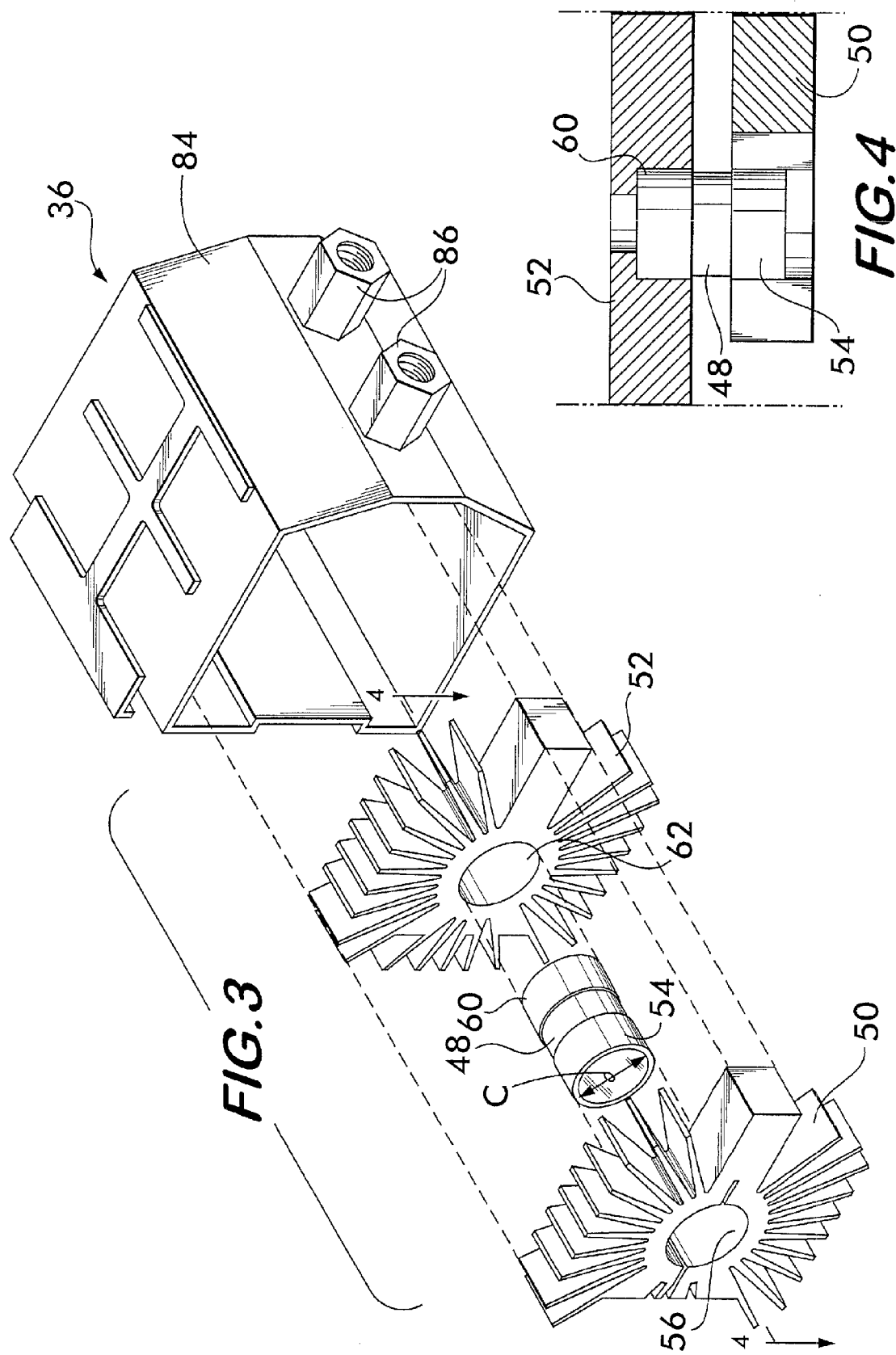

FIBEROPTIC ILLUMINATOR

BACKGROUND OF THE INVENTION

The present invention relates to a fiberoptic illuminator, or light source, for introducing a high intensity light beam into an end of a fiber optic bundle, or cable, and more particularly, the present invention relates to a fiberoptic illuminator for medical applications, such as endoscopic and laparoscopic surgeries or illumination of headlamps worn by surgeons.

Fiberoptic illuminators and like light sources include a lamp within a housing and a jack or port providing a fiber optic cable interface that permits an end fitment of a fiber optic bundle or cable to be connected to the housing. The lamp supplies a light beam into the end of the fiber optic cable, and the cable transmits the light to an endoscope, headlamp, or like medical/surgical device tethered to the illuminator.

Examples of fiberoptic illuminators and light sources in general are provided by U.S. Pat. No. 5,617,302 issued to Kloots; U.S. Pat. No. 5,295,052 issued to Chin et al.; U.S. Pat. No. 5,243,500 issued to Stephenson et al.; U.S. Pat. No. 5,961,203 issued to Schuda; and U.S. Pat. No. 5,329,436 issued to Shiu, and by U.S. patent application Publication No. 2001/0051763 A1 of Kurosawa et al.

Although the above referenced fiberoptic illuminators and light sources may be satisfactory for their intended purposes, there is a need for a fiberoptic illuminator that is of a size and form preferred and accepted by the medical light source market and that provides a source of light of greater intensity then is currently available. In addition, the fiberoptic illuminator should be low noise, should efficiently handle internal heat management issues, and should prevent heat-related damage to the ends of the fiber optic cables. For example, a turret to which the fiber optic cables connect should remain no more than warm to the touch after hours of continuous operation.

BRIEF SUMMARY OF THE INVENTION

According to the present invention, a fiberoptic illuminator has a housing with an interface enabling an end fitting of a fiber optic bundle of a medical device to be connected to the housing. The illuminator includes a lamp assembly mounted within the housing for directing a high intensity beam of light into the fiber optic bundle via an optical assembly. The lamp assembly includes a ceramic xenon lamp of greater than 300 watts. Preferably, the ceramic xenon lamp is at least 400 watts.

According to one contemplated embodiment of the present invention, the fiberoptic illuminator has a housing including front, rear, top and base walls and opposite first and second sidewalls. The lamp assembly is mounted within the housing adjacent the first sidewall and includes a 400 watt ceramic xenon lamp. A fan is mounted within the housing behind the lamp assembly adjacent the first sidewall and an air exchange grate in the rear wall of the housing. An optical assembly is mounted in front of the lamp assembly and includes an infrared filter and focusing lens to collect light and direct it at an opening of a light port formed in the front wall of the housing.

A tunnel-like structure is provided between the fan and lamp assembly enabling a flow of ambient air to be forced to pass over the lamp assembly and out the air exchange grate adjacent the fan. A power supply module controls a supply of power to the lamp and fan and is mounted within the housing adjacent the second sidewall. An air exchange inlet is formed in the second sidewall through which the flow of ambient air is initially drawn into the housing by action of the fan. The flow of ambient air flows over and under the power supply module before passing through the lamp assembly and then out of the housing.

A turret is mounted on an exterior side of the front wall of the housing and receives light directed by the optical assembly through the light port. The turret provides an interface to an end fitting of a bundle of optic fibers of a medical device.

BRIEF DESCRIPTION OF THE DRAWINGS

The features and advantages of the present invention should become apparent from the following description when taken in conjunction with the accompanying drawings, in which:

FIG. 3 is an exploded perspective view of the lamp support and heat sink assembly of FIG. 2;

FIG. 4 is a cross-sectional view along line 4-4 of FIG. 3; and

DETAILED DESCRIPTION OF THE INVENTION

Figure 1:
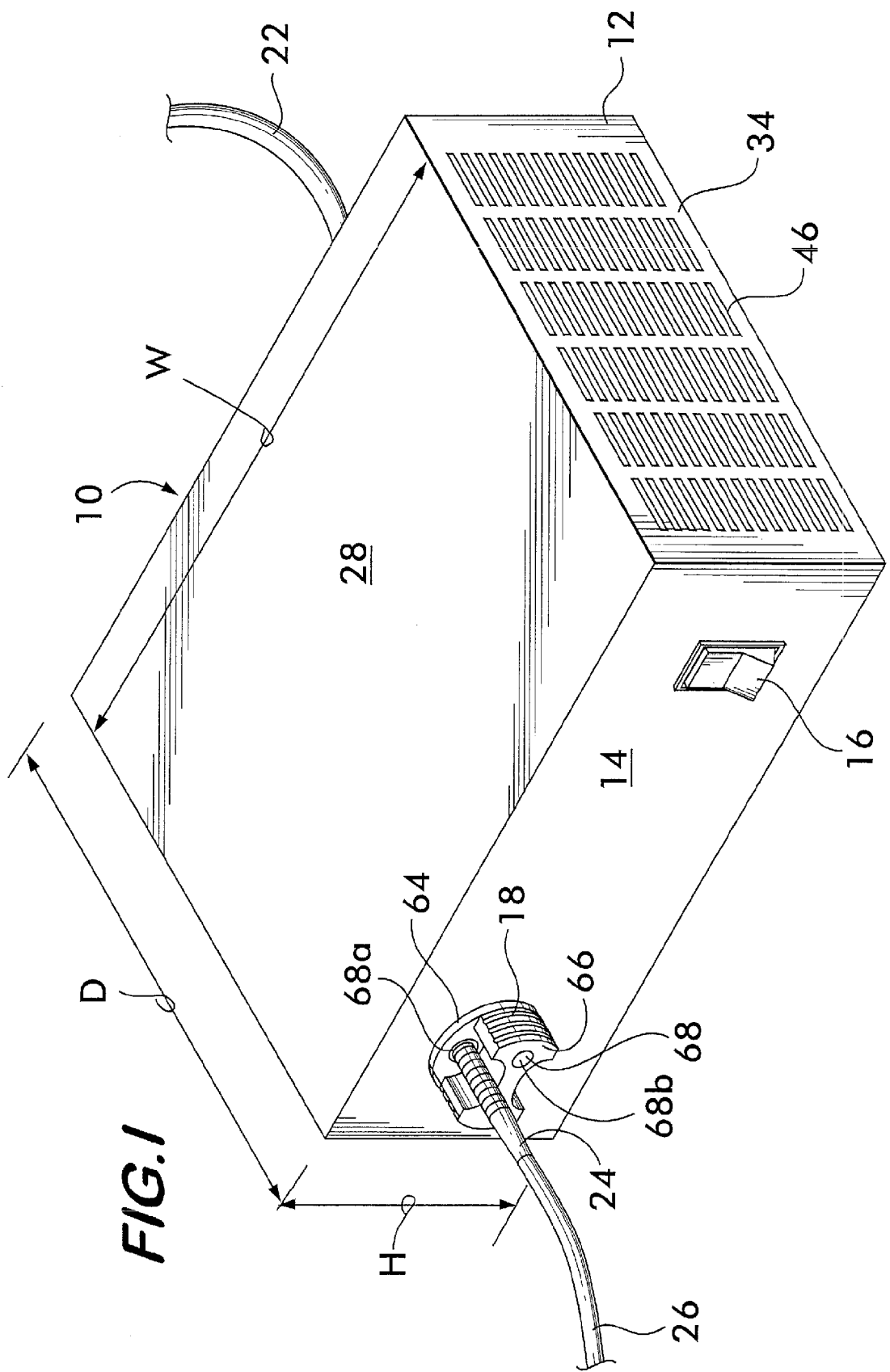
FIG. 1 is a perspective view of a light source unit according to the present invention.

FIG. 1 illustrates a fiberoptic illuminator, or light source, 10 according to the present invention. The fiberoptic illuminator 10 includes a housing 12 of a conventional generally-rectangular, box-shaped configuration having dimensions consistent with currently available illuminators. As an example, the illuminator 10 can be provided with a width "W" of about 14 inches, a height "H" of about 5 inches, and a depth "D" of about 10 inches. Of course, other housing shapes and configurations and dimensions can be utilized provided that the illuminator is of a relatively small size occupying only a relatively small amount of space in an operating room or like environment.

Preferably, the housing 12 is constructed of metal or like walls including a front wall 14 on which an on/off switch 16 and turret 18 are mounted and a rear wall 20 from which a power cord 22 extends. The power cord 22 is adapted to be plugged into a standard AC outlet to provide electrical power to the illuminator 10, and the turret 18 provides an interface mechanism for an end fitting 24 of a cable 26 of a bundle of optic fibers. The cable 26 transmits light from the illuminator 10 to an endoscope, headlamp, or like medical/surgical device tethered to the illuminator 10 via the cable 26. Alternate arrangements of switches, turrets and power cords can be utilized.

Figure 2:
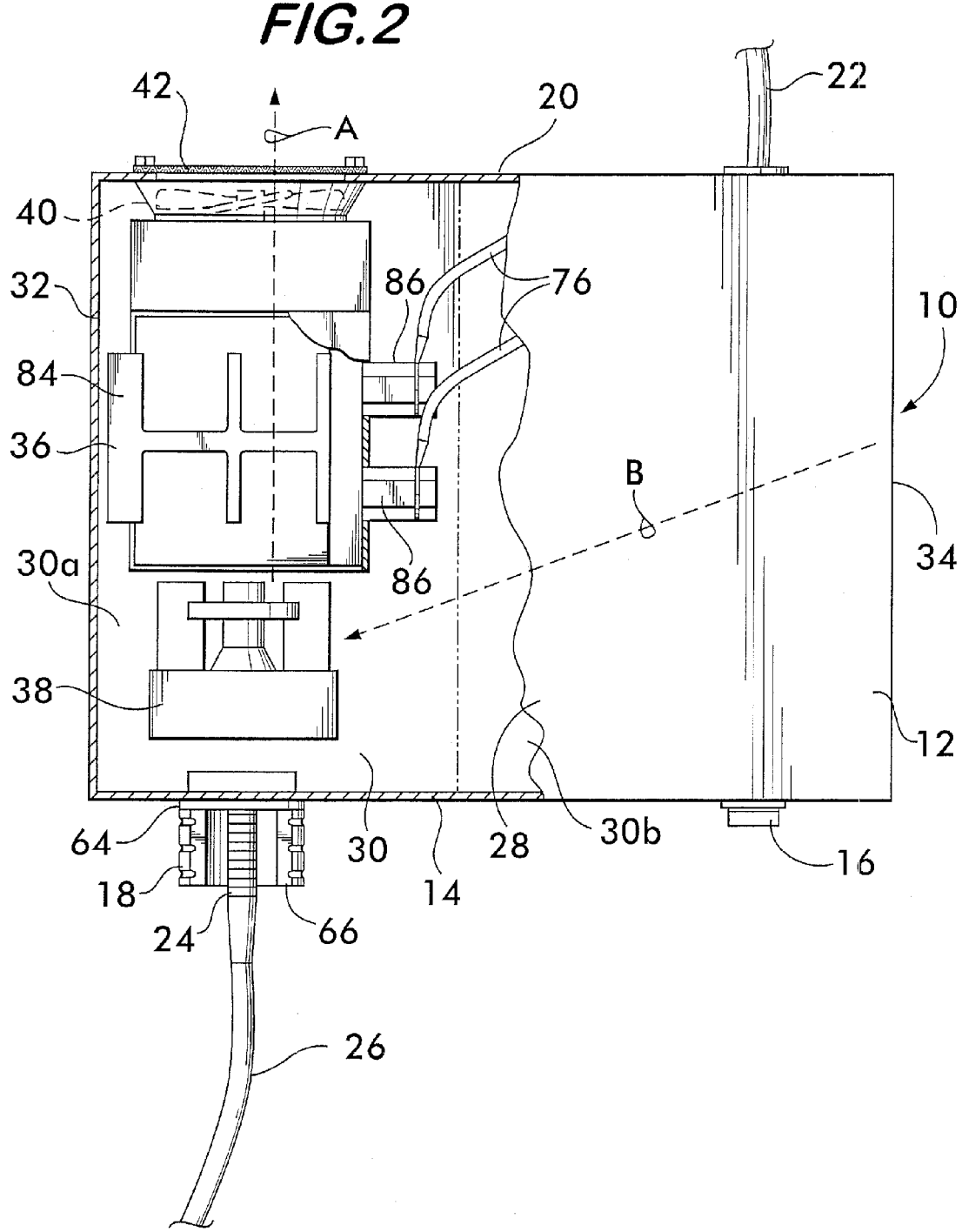
FIG. 2 is a partially cut-away plan view of the light source of FIG. 1.

The housing 12 also includes top and base walls, 28 and 30, and a pair of opposed sidewalls, 32 and 34. As best illustrated in FIG. 2, an optics assembly 38, lamp assembly 36, and fan 40 extend directly behind the turret 18 adjacent the sidewall 32. An air exchange outlet grate 42 is mounted within an opening in the rear wall 20 and permits a flow of ambient air drawn by operation of the fan 40 to pass over and cool the lamp assembly 36 before exiting the housing 12 via the rear wall 20. See arrow "A" in FIG. 2.

The lamp assembly 36 includes a lamp 48, a front heat sink 50, a rear heat sink 52, and a non-conductive housing, or cartridge, 84. The heat sinks 50 and 52 reside within the non-conductive housing 84 and support the lamp 48 therein. The non-conductive housing 84 aligns, supports, and insulates the heat sinks 50 and 52. See FIG. 3. In addition, the non-conductive housing, or cartridge, 84 provides a tunnel-like structure that interconnects with the fan 40 and ensures that the flow of ambient air impinges on the exposed surfaces of the heat sinks, 50 and 52, and lamp 48 before being forced out of the housing 12 by operation of the fan 40.

The lamp 48 according to the present invention is preferably a high intensity xenon lamp greater than 300 watts. More preferably, the lamp 48 is a 400 watt ceramic xenon lamp that has a diameter "C" of about 25 mm and that has cathode and anode ends of equal size. See FIG. 3.

The front, or cathode, side 54 of the lamp 48 is secured within a central opening 56 within the front heat sink 50, and the rear, or anode, side 60 of the lamp 48 is secured within a central opening 62 in the rear heat sink 52. The heat sinks 50 and 52 are provided as separate, relatively-large blocks of metal each having a plurality of spaced-apart, heat-dissipating fins extending radially-outward from the central openings, 56 and 62. The heat sinks 50 and 52 are mounted within the non-conductive housing 84 such that they are spaced from one another and an air gap is formed therebetween.

The lamp assembly 36 is electrically connected to power supply circuitry 44 via plugs 86 and a bracket and wire harness 76. A circuit board or module (not shown) supports the power supply circuitry 44 and is mounted within the housing 12 adjacent the sidewall 34 opposite from the lamp assembly 36, optical assembly 38 and fan 40. For example, the circuitry 44 resides between the on/off switch 16 and power cord 22 as illustrated in FIG. 2.

An air exchange inlet 46, such as provided by slots or a grate, is formed in the sidewall 34 and/or in a portion 30b of the base wall 30 located directly underneath the power supply circuitry 44. The remaining walls of the housing 12 including the front wall 14, sidewall 32, and a portion 30a of the base wall 30 extending under the lamp assembly 36 are substantially solid. Accordingly, upon operation of the fan 40, air within the housing 12 is forced out of the housing 12 through of the grate 42 in the rear wall 20 of the housing, and fresh ambient air is drawn into the housing 12 via inlets 46 in the sidewall 34 and/or base wall 30. The ambient air flows over and under the power supply circuitry 44 and other electrical components (see arrow "B" in FIG. 2) and then through the non-conductive housing, or cartridge, 84 of the lamp assembly 36 (see arrow "A" in FIG. 2). This controlled, forced flow of air enables the housing 12 and its contents to remain within suggested temperature operating limits.

The optics assembly 38 resides between the lamp assembly 36 and the front wall 14 of the housing 12. This assembly provides an infrared filter and focusing lens which collect light generated by the lamp 48 and direct it toward an aperture in the front wall 14 about which the turret 18 is mounted. In use, light generated by the lamp 48 is directed through the aperture in the front wall 14, into at least one of several ports extending through the turret 18, and into the fiber optic cable 26 connected to the turret 18.

Turret 18 dissipates heat and must remain no more than warm to the touch after hours of continuous use of the illuminator. The turret 18 has a base 64 mounted adjacent to the front wall 14 of the housing 12 and a "bow-tie" shaped body 66 extending forward from the base 64. The mass of the base 64 and body 66 provides a heat sink that is able to dissipate the heat energy imparted on the turret 18 by the 400 watt ceramic xenon lamp 48. As an example, the turret can be made of metal or other material. In addition, preferably the base 64 is rotatably mounted to the front wall 14 of the housing 12 enabling different ports 68 of the turret 18 to be aligned with the light projected through the aperture formed in the front wall 14 of the housing 12. The different ports 68 are of various sizes enabling different sized and shaped end fittings of different cable manufacturers to be connected to the illuminator 10 of the present invention. In the illustrated embodiment, a pair of ports 68a extends solely through the base 64 at a location laterally spaced from the body 66, and a pair of ports 68b extends directly through the body 66 and base 64 of the turret 18.

Figure 5:
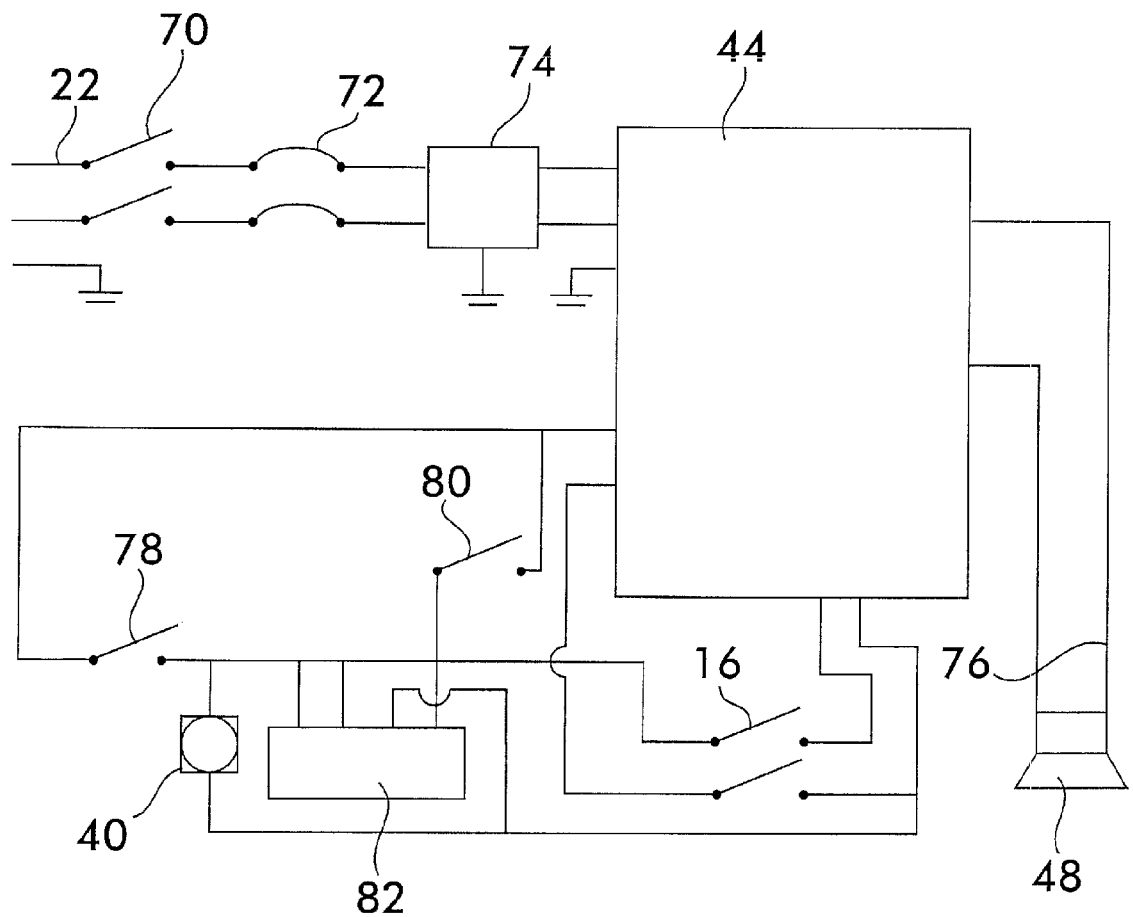
FIG. 5 is an electronic schematic view of the light source according to the present invention.

FIG. 5 schematically illustrates the interconnections of the various electronic components of the illuminator 10. The power cord 22 electrically interconnects to the power supply circuitry, or module, 44 via a power switch 70, circuit breakers 72, and an EMI filter 74. The power supply module 44 provides power to the lamp 48 via wiring 76. The on/off switch 16 and limit switch 78 control the operation of the lamp 48 via the power supply module 44. The power supply module 44 also controls the operation of the fan 40 and a lamp operation hour meter 82, which can be zeroed by a reset switch 80.

Various modifications can be made to the illuminator 10 according to the present invention. For example, a plastic injection molded front panel (not shown) can be secured to the front panel 14 of the housing 12 to provide a desired aesthetic appearance providing flexibility with respect to marketing the illuminator. Further, the arrangement of parts and/or the overall configuration of the unit can be modified provided that air flow through the housing enables the use of a low noise fan and ensures the power supply module and lamp are adequately cooled.

While a preferred light source unit has been described in detail, various modifications, alternations, and changes may be made without departing from the spirit and scope of the light source according to the present invention as defined in the appended claims.

The invention claimed is:

1. A fiberoptic illuminator, comprising:
  a housing having an interface for connecting an end fitting of a fiber optic bundle to said housing;
  a lamp assembly mounted within said housing for directing a high intensity beam of light into the fiber optic bundle, said lamp assembly including only a single ceramic xenon lamp of at least 400 watts, said ceramic xenon lamp having a ceramic body with a diameter of about 25 mm, opposite cathode and anode ends of equal size, and a window at one end; and
  an optics assembly mounted within the housing between the lamp assembly and interface.

2. A fiberoptic illuminator comprising:
  a housing having an interface for connecting an end fitting of a fiber optic bundle to said housing;
  a lamp assembly mounted within said housing for directing a high intensity beam of light into the fiber optic bundle, said lamp assembly including a ceramic xenon lamp, front and rear heat sinks for supporting said lamp, and a non-conductive cartridge in which said heat sinks are mounted, said ceramic xenon lamp being of greater than 300 watts and said cartridge aligning, supporting and insulating said heat sinks within said housing;
  an optics assembly mounted within the housing between the lamp assembly and interface; and
  a fan for drawing a flow of ambient air into said housing and through said cartridge, said fan being mounted behind said cartridge and adjacent an air exchange outlet grate in a rear wall of said housing, and said cartridge and fan forming a tunnel in which the flow of ambient air is forced to flow before exiting said housing.

3. A fiberoptic illuminator according to claim 2, wherein said ceramic xenon lamp is of at least 400 watts.

4. A fiberoptic illuminator according to claim 3, wherein said ceramic xenon lamp has a wattage of 400 watts.

5. A fiberoptic illuminator according to claim 3, wherein said ceramic xenon lamp has a body with a diameter of no more than about 25 mm.

6. A fiberoptic illuminator according to claim 2, wherein said front heat sink is interconnected to a cathode side of said lamp and said rear heat sink is spaced from said front heat sink and interconnects to an anode side of said lamp.

7. A fiberoptic illuminator according to claim 2, wherein said front and rear heat sinks each include a plurality of spaced-apart, radially extending, heat-dissipating fins.

8. A fiberoptic illuminator according to claim 2, further comprising a power supply module mounted within said housing for controlling power provided to said lamp and for controlling operation of said lamp and fan.

9. A fiberoptic illuminator according to claim 8, wherein said housing includes opposite sidewalls, wherein said lamp assembly, optics assembly, and fan are adjacent one of said sidewalls and wherein said power supply module is located adjacent an opposite one of said sidewalls.

10. A fiberoptic illuminator according to claim 9, wherein said sidewall adjacent said power supply module has an air exchange inlet permitting ambient air to be drawn into said housing by operation of said fan and pass over and under said power supply module to cool said module before passing through said cartridge and exiting said housing.

11. A fiberoptic illuminator according to claim 10, wherein said interface includes a turret mounted on an exterior side of said front wall of said housing for receiving light generated by said lamp and directed by said optics assembly through an aperture in said front wall of said housing.

12. A fiberoptic illuminator according to claim 11, wherein said turret includes a base plate and a body portion, said base plate is positioned adjacent said housing, and said body portion extends forward from said base plate.

13. A fiberoptic illuminator according to claim 12, wherein said turret has a plurality of different sized ports, wherein at least one of said ports extends solely through said base plate, and wherein at least one of said ports extends though said base plate and body portion.

14. A fiberoptic illuminator according to claim 13, wherein said turret is made of metal for dissipating heat generated by said lamp.

15. A fiberoptic illuminator, comprising:
   a housing having front, rear, top and base walls and first and second sidewalls;
   a lamp assembly mounted within said housing adjacent said first sidewall, said lamp assembly including a ceramic xenon lamp of no less than 400 watts;
   an optics assembly mounted within the housing adjacent said first sidewall and in front of said lamp assembly;
   a fan mounted within said housing adjacent said first sidewall and an air exchange outlet in said rear wall;
   a tunnel formed adjacent said first sidewall between said fan and lamp assembly for directing a flow of ambient air drawn into said housing by operation of said fan through said lamp assembly;
   a power supply module for controlling a supply of power to said lamp and fan, said module being mounted within said housing adjacent said second sidewall, and said second sidewall and base wall having air exchange inlets through which the flow of air is drawn into said housing by operation of said fan; and
   a turret mounted on an exterior side of said front wall of said housing for receiving light directed through an aperture in said front wall of said housing from said optics assembly and for providing an interface to an end fitting of a bundle of fiber optics.

16. A fiberoptic illuminator according to claim 15, wherein said ceramic xenon lamp has a body with a diameter of about 25 mm.

17. A fiberoptic illuminator according to claim 16, wherein said lamp assembly includes a front heat sink and a rear heat sink for supporting said lamp within said housing, and wherein said front heat sink is interconnected to a cathode side of said lamp and said rear heat sink is spaced from said front heat sink and interconnects to an anode side of said lamp.

18. A fiberoptic illuminator according to claim 17, wherein said front and rear heat sinks each include a plurality of spaced-apart, radially extending, heat-dissipating fins, and wherein said front and rear heat sinks are mounted within a non-conductive cartridge that aligns supports and insulates said heat sinks within said housing.

19. A fiberoptic illuminator according to claim 15, wherein said turret includes a base plate and a body portion, said base plate is positioned adjacent said housing, and said body portion extends forward from said base plate.

20. A fiberoptic illuminator according to claim 19, wherein said turret has a plurality of different sized ports, wherein at least one of said ports extends solely through said base plate, and wherein at least one of said ports extends through said base plate and body portion.

* * * * *